US008058497B2

(12) United States Patent
Cao (10) Patent No.: US 8,058,497 B2
(45) Date of Patent: *Nov. 15, 2011

(54) REDUCING DELETERIOUS EFFECTS OF ALDEHYDES IN OXYGENATES TO OLEFINS REACTIONS WITH CATALYSTS CONTAINING BASIC METAL OXIDES

(75) Inventor: Guang Cao, Branchburg, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 433 days.

This patent is subject to a terminal disclaimer.

(21) Appl. No.: 12/047,878

(22) Filed: Mar. 13, 2008

(65) Prior Publication Data

US 2009/0234171 A1 Sep. 17, 2009

(51) Int. Cl.
*C07C 1/00* (2006.01)
*C07C 2/02* (2006.01)

(52) U.S. Cl. ........ 585/502; 585/638; 585/639; 585/640; 502/208; 502/214; 502/302

(58) Field of Classification Search ................ 585/502, 585/638, 639, 640; 502/208, 214, 302
See application file for complete search history.

(56) References Cited

U.S. PATENT DOCUMENTS

| 4,592,806 A | 6/1986 | Ilgner et al. |
| 6,444,712 B1 | 9/2002 | Janda |
| 6,486,219 B1 | 11/2002 | Janda et al. |
| 2002/0147376 A1* | 10/2002 | Fung et al. ............ 585/638 |
| 2004/0030213 A1* | 2/2004 | Levin et al. ............ 585/640 |
| 2005/0250864 A1* | 11/2005 | Janssen .............. 518/716 |
| 2006/0135834 A1* | 6/2006 | Xu et al. .............. 585/639 |

OTHER PUBLICATIONS

U.S. Appl. No. 11/855,476, filed Sep. 14, 2007, Levin et al.
IMPCA Methanol Reference Specifications, IMPCA, International Methanol Producers & Consumers Assocation, 2004, pp. 1-9.

\* cited by examiner

*Primary Examiner* — Prem C Singh
(74) *Attorney, Agent, or Firm* — Kevin M. Faulkner; David M. Weisberg (57) ABSTRACT

The present invention relates to processes for converting a mixed alcohol feedstock, including methanol and a higher alcohol, to olefins such as ethylene, propylene, and the like. In addition, the olefins produced by the oxygenate-to-olefin reaction system can then be used as monomers for a polymerization of olefin-containing polymers and/or oligomers.

11 Claims, 2 Drawing Sheets

REDUCING DELETERIOUS EFFECTS OF ALDEHYDES IN OXYGENATES TO OLEFINS REACTIONS WITH CATALYSTS CONTAINING BASIC METAL OXIDES

FIELD OF THE INVENTION

The present invention relates to processes for forming olefins from oxygenates containing a first alcohol, such as methanol, as well as one or more other alcohols and/or aldehydes, and processes for producing polyolefins therefrom.

BACKGROUND OF THE INVENTION

Light olefins, defined herein as ethylene and propylene and optionally butylene, are important commodity petrochemicals useful in a variety of processes for making plastics and other chemical compounds. Ethylene is used to make various polyethylene plastics, and in making other chemicals vinyl chloride, ethylene oxide, ethyl benzene and alcohol. Propylene is used to make various polypropylene plastics, and in making other chemicals such as acrylonitrile and propylene oxide.

The petrochemical industry has known for some time that oxygenates, especially alcohols, are convertible into light olefins. The preferred conversion process is generally referred to as an oxygenate-to-olefin (OTO) reaction process. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene.

Methanol is one of the major chemical raw materials, ranking third in volume behind ammonia and ethylene. Worldwide demand for methanol as a chemical raw material continues to rise especially in view of its increasingly important role (along with dimethyl ether) as a source of olefins such as ethylene and propylene and as an alternative energy source, for example, as a motor fuel additive or in the conversion of methanol to gasoline.

Methanol (as well as dimethyl ether) can be produced via the catalytic conversion of a gaseous feedstock comprising hydrogen, carbon monoxide and carbon dioxide. Such a gaseous mixture is commonly referred to as synthesis gas or "syngas".

Methanol is typically produced from the catalytic reaction of syngas in a methanol synthesis reactor in the presence of a heterogeneous catalyst. For example in one synthesis process, methanol is produced using a copper/zinc catalyst in a water-cooled tubular methanol reactor. In methanol production, syngas undergoes three reactions, only two of which are independent. These reactions are:

$$CO + 2H_2 \rightarrow CH_3OH \tag{A}$$

$$CO_2 + 3H_2 \rightarrow CH_3OH + H_2O \tag{B}$$

$$H_2O + CO \leftrightarrow H_2 + CO_2 \tag{C}$$

As can be seen from Reactions B and C, $CO_2$ can participate in methanol synthesis. Nevertheless, it is desirable to minimize the amount of $CO_2$ in the syngas for several reasons. In the first place, a low $CO_2$ content in the syngas results in a more reactive mixture for methanol synthesis provided the $CO_2$ content is at least about 2%. Furthermore, less $CO_2$ results in lower consumption of hydrogen and lower production of water. Lower water production is useful in applications where some relative small amounts of water can be present in the methanol product such as, for example, in connection with a methanol to olefins (MTO) process. Production of methanol with low water content thus eliminates the need to distill water from the syngas product methanol.

The syngas stoichiometry for methanol synthesis from syngas is generally described by the following relationship known as the "Stoichiometric Number" or $S_N$.

$$S_N = (H_2 - CO_2)/(CO + CO_2) \tag{D}$$

The value of $S_N$ theoretically required for methanol synthesis is 2.0. However, for commercial production of methanol from syngas, it is desirable that the value for $S_N$ range from about 1.95 to 2.15. Dimethyl ether (DME) may also be produced from syngas using chemistry similar to that used for methanol synthesis.

For example, U.S. Pat. Nos. 6,444,712 and 6,486,219 both describe methods for producing olefins from methanol, by way of using natural gas to make the methanol. The methods include converting the methane component of the natural gas to synthesis gas (syngas) using a steam reformer and a partial oxidation reformer. The syngas from each reformer is combined and sent to a methanol synthesis reactor. The combined syngas stream to the methanol synthesis reactor desirably has a syngas number of from about 1.4 to 2.6. The methanol product is then used as a feed in a methanol to olefin production process.

Autothermal reforming (ATR) involves the addition of air or oxygen with relatively smaller proportions of steam to a hydrocarbon feedstock. Reaction of hydrocarbon with oxygen proceeds according to the following general reaction schemes:

$$C_nH_m + (n/2)O_2 \leftrightarrow nCO + (m/2)H_2 \tag{E}$$

$$C_nH_m + (n+m/4)O_2 \leftrightarrow nCO_2 + (m/2)H_2O \tag{F}$$

When methane is the hydrocarbon undergoing oxidative reforming, these reactions become:

$$CH_4 + \tfrac{1}{2}O_2 \leftrightarrow CO + 2H_2 \tag{G}$$

$$CH_4 + 2O_2 \leftrightarrow CO_2 + 2H_2O \tag{H}$$

Autothermal reforming employs both steam reforming and oxidative reforming of the hydrocarbon feed. The exothermic oxidation of the feedstock hydrocarbons generates sufficient heat to drive the endothermic steam reforming reaction over the catalyst bed. The ATR procedure is thus run at relatively high temperatures and pressures with a relatively low steam to carbon ratio. The $CO_2$ content of the syngas from ATR processes, however, is fairly low, as is desirable for methanol synthesis.

Another known reforming process involves primarily partial oxidation of a hydrocarbon feed with an oxygen-containing gas. Catalytic partial oxidation reforming procedures are known; for purposes of this invention, partial oxidation reforming takes place in the absence of a catalyst. Due to the absence of a catalyst, partial oxidation (POX) reforming can operate at very high temperatures with little or no steam addition to the feedstock. Higher pressures than are used in ATR operations can be employed in POX reforming. However, the syngas composition resulting from POX reforming is generally deficient in hydrogen for methanol synthesis, resulting in $S_N$ and $H_2$:CO numbers below 2. On the other hand, the $CO_2$ content of the resulting syngas is generally very low which is below the optimum value for methanol synthesis.

Much of the methanol made today is made under high purity specifications. Grade A and grade AA methanol are commonly produced. U.S. Pat. No. 4,592,806 discloses a process for producing the grade AA methanol. The grade AA methanol has a maximum ethanol content of 10 ppm and is produced using a distillation column.

As the production of methanol continues to increase, and the new commercial uses of methanol also continue to increase, it would be advantageous to produce variable quality methanol streams, which have particular advantages for specific end uses, and which do not have to meet the stringent requirements of Grades AA and A methanol. It would also be beneficial to provide various processes for which the methanol streams would be of particular benefit.

Additionally, in many MTO reaction processes, the largest component of the oxygenate feedstock is methanol. However, relatively small amounts of oxygenates and/or higher alcohols, such as ethanol, can also be present in the feedstock. Some prior art MTO feedstocks have been treated to reduce the amounts of oxygenates and higher alcohols, while other prior art MTO feedstocks have been augmented to increase their relative content of higher alcohols and other oxygenates, for a variety of reasons. As a result, most prior art MTO processes utilize feedstocks that have undergone multiple processing and/or treatment steps to attain a higher proportion of higher alcohols, with respect to methanol.

In addition, when mixed alcohols are used as feedstocks in OTO reaction processes, water and carbon dioxide formation or retention can cause problems with olefin formation, e.g., reduced conversion efficiency. The prior art has recognized the benefit of reduction of water content and carbon dioxide content in OTO feedstock streams, but has taught complex combinations of process steps, creating increased cost and efficiency problems.

Various patent applications have been directed to compositions comprising catalysts such as SAPOs being used with predominantly methanol-based feedstocks. If any ethanol is used in these systems, it is at a very low level, presumably to prevent the appearance of impurities such as acetaldehyde (e.g., which are formed by selective dehydrogenation of ethanol in the presence of many OTO catalyst compositions) in the olefin-containing product.

The present invention, as described below, details a never before seen combination of OTO process conditions and product formation, which can attain significant improvements over the prior art, including lower levels of impurities such as aldehydes (e.g., formaldehyde and/or acetaldehyde).

SUMMARY OF THE INVENTION

One aspect of the invention relates to a process for converting an oxygenate feed to a light olefin product comprising: (a) providing the oxygenate feed comprising a majority of methanol and from about 5 wt % to about 30 wt % of one or more $C_2$-$C_4$ alcohols; (b) providing a catalyst composition comprising a SAPO catalyst and a basic metal oxide co-catalyst, wherein the SAPO catalyst comprises a CHA framework type, an AEI framework type, or both, and wherein the basic metal oxide co-catalyst absorbs more than 0.03 mg of $CO_2$ per square meter of co-catalyst surface area at about 100° C.; and (c) contacting the oxygenate feed with the catalyst composition under conditions sufficient to convert at least a portion of the oxygenate feed to a light olefin product, wherein the catalyst composition has an on-stream catalyst lifetime of at least 60 g methanol converted per gram of sieve.

Another aspect of the invention relates to a process for forming olefin-containing (co)polymers from an oxygenate feed comprising the steps of: (a) converting the oxygenate feed to a light olefin product according to any of the previous embodiments; (b) polymerizing at least a portion of the light olefin product as monomer, optionally in combination with one or more other comonomers, under reaction conditions sufficient to polymerize at least 10 wt % of the total amount of monomers and other comonomers to form an olefin-containing (co)polymer product; and optionally (c) washing, isolating, and/or purifying said olefin-containing (co)polymer product to form an olefin-containing (co)polymer.

When process steps are enumerated by alphanumeric characters herein, it should be understood that their order in the recited process need not be set by the sequential nature of the list, i.e., sequential numbers/letters do not necessarily enumerate sequential steps.

Further, as described herein, it is contemplated that embodiments listed separately, even in different aspects of the invention described herein, may be combined together with one or more other embodiments, provided that the embodiments do not have features that are mutually exclusive.

DETAILED DESCRIPTION OF THE INVENTION

A. INTRODUCTION

An oxygenate feedstock, particularly a mixed alcohol composition containing methanol and one or more higher alcohols, is a useful feedstock for a variety of catalytic processes, particularly oxygenate to olefin (OTO) reaction processes, in which a catalyst composition, typically containing a primary oxide catalyst having at least two of Al, Si, and P (e.g., an aluminosilicate molecular sieve, preferably a high-silica aluminosilicate molecular sieve) and preferably a basic metal oxide co-catalyst, can be used to convert the oxygenate feedstock into a light olefin product, e.g., containing ethylene and/or propylene, preferably including ethylene. The olefins can then recovered and used for further processing, e.g., in the manufacture of polyolefins such as polyethylene and/or polypropylene, olefin oligomers, olefin copolymers, mixtures thereof, and/or blends thereof.

Coking rate and coke selectivity are believed to affect (typically in a direct manner) catalyst lifetime in hydrocarbon conversion processes such as OTO, methanol-to-olefins (MTO), and methanol-to-gasoline (MTG). When the coking rate is reduced, the benefits to such conversion processes can include, but are not limited to higher product selectivity, lower regeneration load, and longer catalyst service time, inter alia.

Formaldehyde can tend to form (typically in relatively small quantities) under many conditions during MTO conversion and can contribute to coking. The deleterious effect of aldehydes such as formaldehyde can be mitigated with basic metal oxides, such as $Y_2O_3$. In addition, the catalyst lifetime can be improved, and the coke selectivity of the catalyst accordingly reduced, by including higher alcohols with methanol in the oxygenate feed. In alternate embodiments, the higher alcohols may be present in an already-existing "dirty" methanol feedstock, or the higher alcohols may be deliberately added to a relatively pure methanol feedstock.

As used herein, the terms "catalyst lifetime," "on-stream catalyst lifetime," and "catalyst conversion efficiency" should be understood to refer to the number of grams of MeOH converted per gram of molecular sieve.

B. METHANOL AND MIXED ALCOHOL SYNTHESIS SYSTEMS

There are numerous technologies available for producing methanol including fermentation or the reaction of synthesis gas (syngas) derived from a hydrocarbon feed stream, which may include natural gas, petroleum liquids, carbonaceous materials including coal, recycled plastics, municipal waste, or any other organic material.

The hydrocarbon feed stream that is used in the conversion of hydrocarbon to syngas is optionally treated to remove impurities that can cause problems in further processing of the hydrocarbon feed stream. These impurities can poison many conventional propylene and ethylene forming catalysts. A majority of the impurities that may be present can be removed in any conventional manner. The hydrocarbon feed is preferably purified to remove sulfur compounds, nitrogen compounds, particulate matter, other condensables, and/or other potential catalyst poisons prior to being converted into syngas.

As mentioned above, the hydrocarbon feed stream may be supplied and/or purified by any conventional means of syngas production, including, for example, autothermal reforming, partial oxidation, steam or $CO_2$ reforming, or a combination of these chemistries. Methanol and mixed alcohol feedstock compositions and processes for forming same are disclosed, for example, in commonly-owned, co-pending U.S. Publication No. 2007-0259972 A1 entitled "Process for the Production of Mixed Alcohols", the disclosure of which is fully incorporated herein by reference.

C. OXYGENATE-TO-OLEFIN CONVERSION PROCESS

1. General Process Description

In one embodiment, the mixed alcohol product composition obtained according to this invention comprises at least a portion of an oxygenate feedstock that is converted to olefin(s) via contact with an olefin forming catalyst to form the olefin product. The olefin product can then be recovered, and water, which generally forms during the conversion of the oxygenate(s) in the mixed alcohol composition to olefins, can advantageously be removed. After removing the water, the olefins can be separated into individual olefin streams, with each individual olefin stream being available for further processing, if desired.

Although the present application specifically describes combining a methanol/higher alcohol synthesis system with an OTO reaction system, one or more additional components may be included in the feedstock that is directed to the OTO reaction system. For example, the feedstock that is directed to the OTO reaction system optionally contains, in addition to methanol and a higher alcohol, one or more aliphatic-containing compounds such as other alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to 50 carbon atoms, preferably from 1 to 20 carbon atoms, more preferably from 1 to 10 carbon atoms, most preferably from 1 to 4 carbon atoms.

Non-limiting examples of aliphatic-containing compounds include: alcohols such as methanol, ethanol, n-propanol, isopropanol, and the like, alkyl-mercaptans such as methyl mercaptan and ethyl mercaptan, alkyl-sulfides such as methyl sulfide, alkyl amines such as methyl amine, alkyl ethers such as DME, diethyl ether and methyl ethyl ether, alkyl-halides such as methyl chloride and ethyl chloride, alkyl ketones such as dimethyl ketone, alkyl-aldehydes such as formaldehyde and acetaldehyde, and various organic acids such as formic acid and acetic acid.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene. Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers can include, but are not limited to, unsaturated monomers, diolefins having 4 to 18 carbon atoms, conjugated or nonconjugated dienes, polyenes, vinyl monomers, and cyclic olefins.

In a preferred embodiment, the feedstock, which contains methanol and ethanol, can be converted to olefin(s) having 2 to 6 carbons atoms, preferably 2 to 4 carbon atoms, more preferably at least including light olefin(s) (i.e., ethylene and/or propylene), in the presence of a molecular sieve catalyst composition. The most preferred process is generally referred to as an oxygenates-to-olefins (OTO) reaction process. In an OTO process, typically an oxygenated feedstock, most preferably a methanol- and ethanol-containing feedstock, is converted in the presence of a molecular sieve catalyst composition into one or more olefins, preferably and predominantly including ethylene and/or propylene.

In one embodiment, the amount of methanol in the feedstock for the OTO reaction can advantageously be at least about 45 wt %, preferably at least about 50 wt %, for example at least about 60 wt %, at least about 70 wt %, at least about 75 wt %, at least about 80 wt %, at least about 85 wt %, at least about 90 wt %, or at least about 95 wt %, based on the total weight of feedstock and/or the total weight of the oxygenates in the feedstock (including any diluent contained therein). In one embodiment, the amount of methanol in the feedstock for the OTO reaction can preferably be less than about 97 wt %, for example less than about 95 wt %, less than about 90 wt %, less than about 85 wt %, less than about 80 wt %, less than about 75 wt %, or less than about 70 wt %, based on the total weight of feedstock and/or the total weight of the oxygenates in the feedstock (including any diluent contained therein).

In one embodiment, the amount of the higher alcohol in the feedstock for the OTO reaction can advantageously be at least about 3 wt %, preferably at least about 5 wt %, for example at least about 8 wt %, at least about 10 wt %, at least about 12 wt %, at least about 15 wt %, at least about 17 wt %, at least about 20 wt %, or at least about 25 wt %, based on the total weight of feedstock and/or the total weight of the oxygenates in the feedstock (including any diluent contained therein). In one embodiment, the amount of the higher alcohol in the feedstock for the OTO reaction can be less than about 55 wt %, preferably less than 50 wt %, for example less than 45 wt %, less than 40 wt %, less than 35 wt %, less than 30 wt %, less than 25 wt %, less than 20 wt %, less than 15 wt %, or less than 10 wt %, based on the total weight of feedstock and/or the total weight of the oxygenates in the feedstock (including any diluent contained therein).

In one embodiment, the oxygenate feedstock comprises from about 5 wt % to about 30 wt % $C_2$-$C_3$ alcohols, preferably from about 8 wt % to about 25 wt % $C_2$-$C_3$ alcohols, for example from about 10 wt % to about 20 wt % $C_2$-$C_3$ alcohols.

In one embodiment, the composition and relative amount(s) of the non-methanol component(s) of the oxygenate feedstock is(are) chosen such that the improvement in catalyst efficiency (as measured in grams methanol converted per gram of sieve) can be at least 20%, preferably at least 25%, for example at least 30%, at least 35%, at least 40%, at least 45%, or even at least 50%, as compared to the catalyst efficiency of an essentially pure (99.5+% by weight) methanol feedstock.

In one embodiment, the amount of liquid feedstock, fed separately or jointly with a vapor feedstock, to a reactor system can be in the range from about 0.1 wt % to about 85 wt %, preferably from about 1 wt % to about 75 wt %, more preferably from about 5 wt % to about 65 wt %, based on the total weight of the feedstock (including any diluent contained therein). The liquid and vapor feedstocks can be of substantially the same composition, or contain varying proportions of the same or different feedstock components, optionally with the same or different diluent.

2. Description of Olefin Forming Catalyst

Any catalyst capable of converting oxygenates to olefins can be used in this invention. Molecular sieve catalysts are preferred. Examples of such catalysts include zeolite-based, as well as non-zeolite-based, molecular sieves and can be of the large, medium, or small pore type. Molecular sieve materials all have 3-dimensional, four-connected framework structure of corner-sharing [$TO_4$] tetrahedra, where T can be any tetrahedrally coordinated cation. These molecular sieves are typically described in terms of the size of the ring that defines a pore, where the size is based on the number of T atoms in the ring. Other framework-type characteristics include the arrangement of rings that form a cage, and, when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B.V., Amsterdam, Netherlands (2001).

Non-limiting examples of molecular sieves include small pore molecular sieves (e.g., AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof), medium pore molecular sieves (e.g., AFO, AEL, EUO, HEU, FER, MEL, MFI, MTW, MTT, TON, and substituted forms thereof), large pore molecular sieves (e.g., EMT, FAU, and substituted forms thereof), intergrowths thereof, and combinations thereof. Other molecular sieves include, but are not limited to, ANA, BEA, CFI, CLO, DON, GIS, LTL, MER, MOR, MWW, SOD, intergrowths thereof, and combinations thereof. Non-limiting examples of preferred molecular sieves, particularly for converting an oxygenate-containing feedstock into olefin(s), can include AEL, AFY, AEI, BEA, CHA, EDI, FAU, FER, GIS, LTA, LTL, MER, MFI, MOR, MTT, MWW, TAM, TON, intergrowths thereof, and combinations thereof. In a preferred embodiment, the molecular sieve has an AEI topology and/or a CHA topology (i.e., including an AEI/CHA intergrowth), most preferably at least containing a CHA topology.

The small, medium, and large pore molecular sieves have from a 4-ring to a 12-ring or greater framework-type. In a preferred embodiment, the zeolitic molecular sieves have 6-, 8-, 10-, or 12-ring structures and an average pore size in the range from about 3 Å to 15 Å. In a more preferred embodiment, the molecular sieves, preferably aluminosilicate molecular sieves, have a 6-ring or an 8-ring structure and advantageously an average pore size less than about 5 Å, such as in the range from 3 Å to about 5 Å, for example from 3 Å to about 4.5 Å or from 3.5 Å to about 4.2 Å.

Other non-limiting examples of zeolitic and non-zeolitic molecular sieves include one or a combination of the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-20, ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245), ZSM-38, ZSM-48 (U.S. Pat. No. 4,397,827), ZSM-50, ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), ultrastable Y zeolite (USY), mordenite, SSZ-13, titanium aluminosilicates (TASOs) such as TASO-45 (European Patent No. EP-A-0 229 295), boron silicates (U.S. Pat. No. 4,254,297), titanium aluminophosphates (TAPOs) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), those disclosed in International Publication No. WO 98/57743 published Dec. 23, 1988 (molecular sieve and Fischer-Tropsch), those disclosed in U.S. Pat. No. 6,300,535 (MFI-bound zeolites), mesoporous molecular sieves (U.S. Pat. Nos. 6,284,696, 5,098,684, 5,102,643 and 5,108,725), and the like, and intergrowths and/or combinations thereof. The entire disclosure of each of the references in this paragraph is hereby fully incorporated by reference herein.

In one embodiment, the molecular sieve catalyst composition comprises an aluminosilicate catalyst composition, preferably a relatively high-silica aluminosilicate catalyst composition. Relatively high-silica aluminosilicates, as used herein, can advantageously include those having a molar relationship of $X_2O_3$:(n)$YO_2$ (wherein X is a trivalent element and Y is a tetravalent element), in which n is at least about 80, preferably at least about 100, for example at least about 120, at least about 150, at least about 180, or at least about 200, and typically not more than about 5000, preferably not more than about 4000, for example not more than about 3500, not more than about 3000, not more than about 2500, or not more than about 2000. Alternatively, n for relatively high-silica aluminosilicates can be from about 300 to about 4000, for example from about 300 to about 2500.

Non-limiting examples of trivalent X can include aluminum, boron, iron, indium, gallium, and combinations thereof, preferably at least including aluminum. Non-limiting examples of tetravalent Y can include silicon, tin, titanium, germanium, and combinations thereof, preferably at least containing silicon.

In embodiments where X represents aluminum and Y represents silicon, the factor n represents a silica:alumina ratio, also termed $Si:Al_2$. Another measure of relative proportion in such cases is the ratio of Y:X, or the silicon:aluminum ratio. In one embodiment, the silicon:aluminum (Si:Al) ratio of relatively high-silica aluminosilicates is at least about 40, preferably at least about 50, for example at least about 60, at least about 75, at least about 90, or at least about 100, and typically not more than about 2500, preferably not more than about 2000, for example not more than about 1750, not more than about 1500, not more than about 1250, or not more than about 1000. Alternatively, the Si:Al ratio of relatively high-silica aluminosilicates can be from about 150 to about 2000, for example from about 150 to about 1250.

Other non-limiting examples of aluminosilicate catalysts and compositions can be found, for instance, in U.S. Patent Application Publication No. 2003/0176751 and U.S. patent application Ser. No. 11/017,286 (filed Dec. 20, 2004) and 60/731,846 (filed Oct. 31, 2005), the disclosures of each of which are incorporated by reference herein.

In a preferred embodiment, the catalyst (molecular sieve) used in this invention can include at least in part a chabazite (CHA) framework, an AEI framework, and/or at least one intergrown phase of a CHA framework and an AEI framework. Intergrown molecular sieve phases can be described as disordered planar intergrowths of molecular sieve frameworks, e.g., as referenced in detail in *Catalog of Disordered Zeolite Structures*, 2000 Edition, published by the Structure Commission of the International Zeolite Association, and in *Collection of Simulated XRD Powder Patterns for Zeolites*, M. M. J. Treacy and J. B. Higgins, 2001 Edition, published on behalf of the Structure Commission of the International Zeolite Association.

Regular crystalline solids are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

Analysis of intergrown molecular sieves, such as AEI/CHA intergrowths, can be effected by X-ray diffraction and in particular by comparing the observed patterns with calculated patterns generated using algorithms to simulate the effects of stacking disorder. DIFFaX is a computer program based on a mathematical model for calculating intensities from crystals containing planar faults (see M. M. J. Tracey et al., *Proceedings of the Royal Chemical Society*, London, A[1991], Vol. 433, pp. 499-520). DIFFaX is the simulation program selected by and available from the International Zeolite Association to simulate the XRD powder patterns for randomly intergrown phases of zeolites (see *Collection of Simulated XRD Powder Patterns for Zeolites*, by M. M. J. Treacy and J. B. Higgins, 2001, Fourth Edition, published on behalf of the Structure Commission of the International Zeolite Association). It has also been used to theoretically study intergrown phases of AEI, CHA, and KFI, as reported by K. P. Lillerud et al. in *Studies in Surface Science and Catalysis*, 1994, Vol. 84, pp. 543-550.

Where the crystalline (catalyst) material of the invention comprises a mixture of CHA and AEI or an intergrowth of a CHA framework and an AEI framework, the material can possess a widely varying AEI/CHA ratio of from about 99:1 to about 1:99, such as from about 98:2 to about 2:98, for example from about 95:5 to about 5:95. In one embodiment, where the material is to be used a catalyst in the conversion of oxygenates to olefins, the intergrowth can preferably be CHA-rich and can advantageously have a AEI/CHA ratio ranging from about 5:95 to less than 50:50, from about 5:95 to about 45:55, from about 5:95 to about 40:60, or alternately from about 5:95 to about 30:70. In addition, in some cases the intergrown material of the invention may comprise a plurality of intergrown phases with a distribution of different AEI/CHA ratios. The relative amounts of AEI and CHA framework-types in the intergrowth can be determined by a variety of known techniques, including, but not limited to, transmission electron microscopy (TEM) and DIFFaX analysis, using the powder X-ray diffraction pattern of a calcined sample of the catalyst.

The catalyst can be incorporated or mixed with other additive materials. Such an admixture is typically referred to as formulated catalyst or as catalyst composition. Preferably, the additive materials are substantially inert to conversion reactions involving dialkyl ethers (e.g., dimethyl ether) and/or alkanols (e.g., methanol, ethanol, and the like).

In one embodiment, one or more other materials can be mixed with the crystalline material, particularly a material that is resistant to the temperatures and other conditions employed in organic conversion processes. Such materials can include catalytically active and inactive materials and synthetic or naturally occurring zeolites, as well as inorganic materials such as clays, silica, and/or other metal oxides such as alumina. The latter may be either naturally occurring or in the form of gelatinous precipitates or gels including mixtures of silica and metal oxides. Use of a catalytically active material can tend to change the conversion and/or selectivity of the catalyst in the oxygenate conversion process. Inactive materials suitably can serve as diluents to control the amount of conversion in the process so that products can be obtained in an economic and orderly manner without employing other means for controlling the rate of reaction. These materials can be incorporated into naturally occurring clays, e.g., bentonite and kaolin, to improve the crush strength of the catalyst under commercial operating conditions. The materials (e.g., clays, oxides, etc.) can function as binders for the catalyst. It can be desirable to provide a catalyst having good crush strength, because, in commercial use, it can be desirable to prevent the catalyst from breaking down into powder-like materials.

Naturally occurring clays that can be employed can include, but are not limited to, the montmorillonite and kaolin family, which families include the subbentonites, and the kaolins commonly known as Dixie, McNamee, Georgia and Florida clays, or others in which the main mineral constituent includes halloysite, kaolinite, dickite, nacrite, or anauxite. Such clays can be used in the raw state as originally mined or initially subjected to calcination, acid treatment, or chemical modification. Other useful binders can include, but are not limited to, inorganic oxides such as silica, titania, beryllia, alumina, and mixtures thereof.

In addition to the foregoing materials, the crystalline material used in this invention can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The relative proportions of crystalline material and inorganic oxide matrix may vary widely. For example, a mixture can include a zeolite content ranging from about 1 to about 90 percent by weight and more usually, particularly when the composite is prepared in the form of beads, in the range from about 2 to about 80 weight percent of the composite.

Additionally or alternately, non-limiting examples of catalyst composition components/materials and/or their relative proportions can be found, e.g., in U.S. Pat. Nos. 5,962,762, 6,004,898, 6,040,264, 6,436,869, 6,448,460, and 6,936,566, inter alia, the disclosures of each of which are fully incorporated herein by reference.

In one embodiment, the catalyst compositions according to the invention can (optionally but preferably) additionally contain an active or "basic" metal oxide co-catalyst. This metal oxide co-catalyst can be present in many forms and, as follows, in varying degrees of increasing proximity to the molecular sieve catalyst and/or the catalyst composition. For instance, the metal oxide co-catalyst can be present as particulate matter separate from the formulated catalyst composition particles. Additionally or alternately, the metal oxide co-catalyst can be present as a component of the formulated catalyst composition particles. Additionally or alternately, the metal oxide co-catalyst can be coated on the surface and/or in the pores of the molecular sieve catalyst itself.

In one embodiment, active metal oxides are those metal oxides, different from typical binders and/or matrix materials, that, when used in combination with a molecular sieve in a catalyst composition, are effective in extending of the useful life of the catalyst composition. Quantification of the extension in catalyst life is determined by the Lifetime Enhancement Index (LEI) as defined by the following equation:

$$LEI = \frac{\text{Lifetime of Catalyst in Combination with Active Metal Oxide}}{\text{Lifetime of Catalyst}}$$

where the lifetime of the catalyst or catalyst composition, in the same process under the same conditions, is the cumulative amount of feedstock processed per gram of catalyst composition until the conversion of feedstock by the catalyst composition falls below some defined level, for example 10%. An inactive metal oxide will have little to no effect on the lifetime of the catalyst composition, or will shorten the lifetime of the catalyst composition, and will therefore have a LEI less than or equal to 1. Thus active metal oxides of the invention are those metal oxides, different from typical binders and/or matrix materials, that, when used in combination with a molecular sieve, provide a molecular sieve catalyst composition that has a LEI greater than 1. By definition, a molecular sieve catalyst composition that has not been combined with an active metal oxide will have a LEI equal to 1.0.

It is found that, by including an active metal oxide in combination with a molecular sieve, a catalyst composition can be produced having an LEI from greater than 1 to about 200, for example from about 1.5 to about 100. Typically catalyst compositions according to the invention can exhibit LEI values greater than 1.1, for example from about 1.2 to about 15, and more particularly greater than 1.3, such as greater than 1.5, such as greater than 1.7, such as greater than 2. In one embodiment, the catalyst composition according to the invention can have an LEI value of at least 3.9, for example from 4.0 to 10.0, from 4.0 to 8.0, from 4.0 to 6.0, from 4.0 to 5.5, from 4.0 to 5.0, or from 4.0 to 4.5.

In one embodiment, the active metal oxide when combined with a molecular sieve in a catalyst composition enhances the lifetime of the catalyst composition in the conversion of a feedstock comprising methanol, preferably into one or more olefin(s).

In one embodiment in which an active metal oxide co-catalyst is present, the metal oxide co-catalyst is a basic metal oxide. One way of determining basicity in metal oxides involves measuring the absorbance of $CO_2$ per surface area of metal oxide at a given temperature, e.g., about 100° C. Without being bound by theory, it is postulated that absorbance of $CO_2$ by the metal oxide indicates the presence of basic sites in the metal oxide and that increasing basicity (or increasing the density of basic sites) of metal oxide typically correlates with increasing $CO_2$ absorbance. For instance, in some embodiments, the metal oxide co-catalyst can absorb more than 0.03 mg of $CO_2$ per square meter of metal oxide surface area at about 100° C., for example more than 0.035 mg of $CO_2$ per square meter of metal oxide surface area at about 100° C., more than 0.04 mg of $CO_2$ per square meter of metal oxide surface area at about 100° C., more than 0.05 mg of $CO_2$ per square meter of metal oxide surface area at about 100° C., or more than 0.1 mg of $CO_2$ per square meter of metal oxide surface area at about 100° C. Alternately or additionally, in some embodiments, the metal oxide co-catalyst can absorb less than 15 mg of $CO_2$ per square meter of metal oxide surface area at about 100° C., for example less than 10 mg of $CO_2$ per square meter of metal oxide surface area at about 100° C., less than 7 mg of $CO_2$ per square meter of metal oxide surface area at about 100° C., less than 5 mg of $CO_2$ per square meter of metal oxide surface area at about 100° C., or less than 4 mg of $CO_2$ per square meter of metal oxide surface area at about 100° C.

In order to determine the carbon dioxide uptake of a metal oxide, the following procedure is adopted. A sample of the metal oxide is dehydrated by heating the sample to about 200° C. to 500° C. in flowing air until a constant weight, the "dry weight", is obtained. The temperature of the sample is then reduced to 100° C. and carbon dioxide is passed over the sample, either continuously or in pulses, again until constant weight is obtained. The increase in weight of the sample in terms of mg/mg of the sample based on the dry weight of the sample is the amount of adsorbed carbon dioxide.

In a preferred embodiment, the carbon dioxide adsorption can be measured using a Mettler TGA/SDTA 851 thermogravimetric analysis system under ambient pressure. Using this apparatus, the metal oxide sample can be dehydrated in flowing air to about 500° C. for one hour. The temperature of the sample can then be reduced in flowing helium to 100° C. After the sample has equilibrated at the desired adsorption temperature in flowing helium, the sample can be subjected to 20 separate pulses (about 12 seconds/pulse) of a gaseous mixture comprising 10 wt % carbon dioxide with the remainder being helium. After each pulse of the adsorbing gas, the metal oxide sample can be flushed with flowing helium for 3 minutes. The increase in weight of the sample, in terms of mg/mg adsorbent, based on the adsorbent weight after treatment at 500° C., typically gives the amount of adsorbed carbon dioxide. The surface area of the sample can be measured in accordance with the method of Brunauer, Emmett, and Teller (BET) published as ASTM D 3663 to provide the carbon dioxide uptake in terms of mg carbon dioxide/$m^2$ of the metal oxide.

In one embodiment, the active metal oxide(s) has(have) a BET surface area of greater than 10 $m^2$/g, such as greater than 10 $m^2$/g to about 300 $m^2$/g. In another embodiment, the active metal oxide(s) has a BET surface area greater than 20 $m^2$/g, such as from greater than 20 m²/g to 250 m²/g. In yet another embodiment, the active metal oxide(s) has a BET surface area greater than 25 m²/g, such as from greater than 25 m²/g to about 200 m²/g. In a preferred embodiment, the active metal oxide(s) has a BET surface area greater than 20 m²/g, such as greater than 25 m²/g, and particularly greater than 30 m²/g.

The active metal oxide(s) used herein can be prepared using a variety of methods. It is preferable that the active metal oxide is made from an active metal oxide precursor, such as a metal salt, such as a halide, nitrate, sulfate, or acetate. Other suitable sources of the metal oxide include compounds that form the metal oxide during calcination, such as oxychlorides and nitrates. In one embodiment, the active metal oxide can be made from a hydrated metal oxide precursor. Hydrated metal oxide precursors, such as hydrated zirconia, are disclosed, for example, in U.S. Pat. No. 6,844,291, which is incorporated herein by reference in its entirety. According to one method, the active metal oxide is prepared by the thermal decomposition of metal-containing compounds, such as magnesium oxalate and barium oxalate, at high temperatures, such as 600° C., in flowing air. Thus prepared metal oxides usually have low BET surface area. In another method, the active metal oxide is prepared by the hydrolysis of metal-containing compounds followed by dehydration and calcination. In yet another method, the active metal oxide is prepared by the so-called aerogel method (Koper, O. B., Lagadic, I., Volodin, A. and Klabunde, K. J. *Chem. Mater.* 1997, 9, 2468-2480). Other aspects of metal oxides and their preparation can be found, e.g., in U.S. Patent Application Publication No. 2003/0171633 A1 and U.S. Pat. No. 6,995,111, the disclosures of each of which are hereby incorporated herein by reference in their entirety.

In one embodiment where hydrated metal oxide precursors are utilized, the hydrated metal oxide precursor can be hydrothermally treated under conditions that include a temperature of at least 80° C., preferably at least 100° C. The hydrothermal treatment typically takes place in a sealed vessel at greater than atmospheric pressure. However, a preferred mode of treatment involves the use of an open vessel under reflux conditions. Agitation of hydrated metal oxides in a liquid medium, for example, by the action of refluxing liquid and/or stirring, can promote the effective interaction of the hydrated oxide with the liquid medium. The duration of the contact of the hydrated oxide with the liquid medium can conveniently be at least 1 hour, such as at least 8 hours. The liquid medium for this treatment typically has a pH of about 6 or greater, such as 8 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

In another embodiment, the active metal oxide is prepared, for example, by subjecting a liquid solution, such as an aqueous solution, comprising a source of ions of a desired metal to conditions sufficient to cause precipitation of a hydrated precursor of the solid oxide material, such as by the addition of a precipitating reagent to the solution. Conveniently, the precipitation can be conducted at a pH above 7. For example, the precipitating agent may be a base such as sodium hydroxide or ammonium hydroxide.

Various methods exist for making mixed metal oxide precursors, e.g., wet impregnation, incipient wetness, and co-precipitation, inter alia.

Non-limiting examples of basic metal oxides include, but are not limited to, hydrotalcite, oxides of metals in Group 2 of the Periodic Table of Elements, oxides of metals in Group 3 of the Periodic Table of Elements, oxides of metals in Group 4 of the Periodic Table of Elements, a mixed metal oxide containing one or more metals of Groups 2, 3, and 4 of the Periodic Table of Elements, or a combination thereof. As used herein, Group 3 metals from the Periodic Table of Elements should be understood to include Lanthanide series metals and Actinide series metals. In one preferred embodiment, the metal oxide co-catalyst comprises an oxide of yttrium. In another preferred embodiment, the metal oxide co-catalyst comprises an oxide of zirconium. In another preferred embodiment, the metal oxide co-catalyst comprises a mixed oxide of yttrium and zirconium. In another preferred embodiment, the metal oxide co-catalyst comprises a mixed oxide of a lanthanide (more preferably, lanthanum) and zirconium. In another preferred embodiment, the metal oxide co-catalyst comprises an oxide of magnesium. In another preferred embodiment, the metal oxide co-catalyst comprises a mixed oxide of a lanthanide (more preferably, lanthanum) and magnesium.

Naturally occurring hydrotalcite is a mineral found in relatively small quantities in a limited number of geographical areas, principally, in Norway and in the Ural Mountains. Natural hydrotalcite has a variable composition depending on the location of the source. Natural hydrotalcite is a hydrated magnesium, aluminum and carbonate-containing composition, which has been found to have the typical composition, represented as $Mg_6Al_2(OH)_{16}CO_3 \cdot 4H_2O$. Natural hydrotalcite deposits are generally found intermeshed with spinel and other minerals, such as penninite and muscovite, from which it is difficult to separate the natural hydrotalcite.

Synthetically produced hydrotalcite can be made to have the same composition as natural hydrotalcite, or, because of flexibility in the synthesis, it can be made to have a different composition by replacing the carbonate anion with other anions, such as phosphate ion. In addition, the Mg/Al ratio can be varied to control the basic properties of the hydrotalcite.

A phosphate-modified synthetic hydrotalcite and a process for its synthesis are disclosed in U.S. Pat. No. 4,883,533. U.S. Pat. No. 3,539,306 discloses a process for preparing hydrotalcite which involves mixing an aluminum-containing compound with a magnesium-containing compound in an aqueous medium in the presence of carbonate ion at a pH of at least 8. U.S. Pat. No. 4,656,156 discloses a process for producing synthetic hydrotalcite by heating a magnesium compound to a temperature of about 500 to 900° C. to form activated magnesia, adding the activated magnesia to an aqueous solution containing aluminate, carbonate and hydroxyl ions, and then agitating the resultant mixture at a temperature of about 80 to 100° C. for 20 to 120 minutes to form a low density, high porosity hydrotalcite. A similar process is disclosed in U.S. Pat. No. 4,904,457. The entire disclosure of each of the above references is incorporated herein by reference.

Hydrotalcite compositions containing pillaring organic, inorganic, and mixed organic/inorganic anions are disclosed in U.S. Pat. No. 4,774,212, the entire disclosure of which is incorporated herein by reference. The compositions are anionic magnesium aluminum hydrotalcite clays having large inorganic and/or organic anions located interstitially between positively charged layers of metal hydroxides. The compositions are of the formula:

$$[Mg_{2x}Al_2(OH)_{4x+4}]Y_{2/n}{}^{n-} \cdot ZH_2O$$

where Y is a large organic anion selected from the group consisting of lauryl sulfate, p-toluenesulfonate, terephthalate, 2,5-dihydroxy-1,4-benzenedisulfonate, and 1,5-naphthalene-disulfonate or where Y is an anionic polyoxometalate of vanadium, tungsten or molybdenum. In the above cases, x is from 1.5 to 2.5, n is 1 or 2 and Z is from 0 to 3, except that, when Y is polyoxometalate, n is 6.

An aggregated synthetic hydrotalcite having a substantially spheroidal shape and an average spherical diameter of up to about 60 μm, composed of individual platy particles, is disclosed in U.S. Pat. No. 5,364,828, the entire disclosure of which is incorporated herein by reference. This form of hydrotalcite is prepared from aqueous solutions of soluble magnesium and aluminum salts, which are mixed in a molar ratio of from about 2.5:1 to 4:1, together with a basic solution containing at least a two-fold excess of carbonate and a sufficient amount of a base to maintain a pH of the reaction mixture in the range of from about 8.5 to about 9.5.

Prior to use in the catalyst composition of the invention, it may be desirable to calcine the hydrotalcite to remove the water inherently contained by the material. Suitable calcination conditions include a temperature of from about 300° C. to about 800° C., such as from about 400° C. to about 600° C. for about 1 to about 16 hours, such as for about 3 to about 8 hours.

In one embodiment, in which a basic metal oxide co-catalyst is present in combination with the molecular sieve catalyst, the weight/weight ratio of molecular sieve catalyst (alone, without binder, matrix, etc.) to basic metal oxide co-catalyst can be from about 100:1 to about 1:2, preferably from about 50:1 to about 1:1, for example from about 25:1 to about 3:2, from about 19:1 to about 3:2, or from about 10:1 to about 2:1.

3. Adding Other Oxygenates to Mixed Alcohol Compositions

In an optional embodiment of this invention, the mixed alcohol composition can be converted into olefin(s) along with other oxygenates or diluents. The additional oxygenates or diluents can be co-mixed with the mixed alcohol composition, or can be added as a separate feed stream to an oxygenate conversion reactor in an OTO process. In one embodiment, the additional oxygenate includes one or more alcohols, preferably aliphatic alcohol(s) where the aliphatic moiety of the alcohol(s) has from 3 to 10 carbon atoms, preferably from 3 to 5 carbon atoms, and most preferably from 3 to 4 carbon atoms. The alcohols include lower straight and branched chain aliphatic alcohols and their unsaturated counterparts. Non-limiting examples of additional oxygenates include n-propanol, isopropanol, methyl ethyl ether, dimethyl ether, diethyl ether, diisopropyl ether, methyl propyl ethers, ethyl propyl ethers, methyl butyl ethers such as methyl t-butyl ether, formaldehyde, dimethyl carbonate, dimethyl ketone, acetic acid, and mixtures thereof In one embodiment, the feedstock for the OTO process can include, aside from methanol and a higher alcohol, one or more of dimethyl ether, diethyl ether, methyl t-butyl ether, acetic acid, or a combination thereof.

The mixed alcohol feedstock, in one embodiment, contains one or more diluent(s), typically used to reduce the concentration of alcohol (predominantly methanol), and are generally substantially non-reactive with the oxygenate(s) in the feedstock and/or with the molecular sieve catalyst composition. Non-limiting examples of diluents include helium, argon, nitrogen, carbon monoxide, carbon dioxide, water, essentially non-reactive paraffins (e.g., alkanes such as methane, ethane, propane, and the like), essentially non-reactive aromatic compounds, and mixtures thereof. In one embodiment, the amount of diluent in the feedstock can be from about 0.1 mol % to about 99 mol %, based on the total number of moles of the feedstock and any added diluent, preferably from about 0.5 mol % to about 80 mol %, for example from about 1 mol % to about 50 mol % or from about 3 mol % to about 25 mol %.

4. General Conditions for Converting Methanol/Higher Alcohol to Olefins

According to the OTO reaction process of the invention, oxygenates can be contacted with an olefin forming catalyst to form an olefin product, particularly a light olefin product such as ethylene and/or propylene. The process for converting a feedstock, especially a feedstock containing one or more oxygenates, in the presence of an olefin-forming molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The OTO reaction processes can take place in a variety of catalytic reactors, for instance, circulating fluidized bed reactors, riser reactors, hybrid reactors that have a dense bed or fixed bed reaction zones and/or fast fluidized bed reaction zones coupled together, and the like. Suitable conventional reactor types can be found, for example, in U.S. Pat. Nos. 4,076,796 and 6,287,522, and in *Fluidization Engineering*, D. Kunii and O. Levenspiel, Robert E. Krieger Publishing Company, New York, N.Y. (1977), which is herein fully incorporated by reference.

One preferred reactor type is a riser reactor. These types of reactors are generally described, for example, in Riser Reactor, Fluidization and Fluid-Particle Systems, pages 48 to 59, F.A. Zenz and D.F. Othmo, Reinhold Publishing Corporation, New York, 1960, in U.S. Pat. No. 6,166,282 (fast-fluidized bed reactor), and in U.S. Pat. No. 7,102,050 which are all herein fully incorporated by reference.

The conversion temperature employed in the conversion process, specifically within the reactor system, is typically from about 392° F. (200° C.) to about 1832° F. (1000° C.). In one embodiment, the average reaction temperature employed in the conversion process, specifically within the reactor, can be from about 482° F. (250° C.) to about 1472° F. (800° C.), preferably from about 482° F. (250° C.) to about 1382° F. (750° C.), for example from about 572° F. (300° C.) to about 1202° F. (650° C.), from about 662° F. (350° C.) to about 1112° F. (600° C.), from about 662° F. (350° C.) to about 1022° F. (550° C.), or from about 752° F. (400° C.) to about 932° F. (500° C.).

The pressure employed in the conversion process, specifically within the reactor, is generally not critical. The reaction pressure can desirably be based on the partial pressure of the feedstock, exclusive of any diluent therein. In one embodiment, the reaction pressure employed in the process ranges from about 0.1 kPaa (kPa absolute) to about 5 MPaa (MPa absolute), preferably from about 5 kPaa to about 1 MPaa, most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock, excluding any diluents, to the reaction zone per hour per weight of molecular sieve in the molecular sieve catalyst composition in the reaction zone. The WHSV can advantageously be maintained at a level sufficient to keep the catalyst composition in a fluidized state within a reactor.

In one embodiment, the WHSV can range from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, most preferably from about 10 $hr^{-1}$ to about 1000 $hr^{-1}$. In a preferred embodiment, the WHSV can be greater than 20 $hr^{-1}$. Where a feedstock containing methanol and dimethyl ether is being converted, the WHSV can, in one embodiment, be from about 20 hr$^{-1}$ to about 300 hr$^{-1}$.

The superficial gas velocity (SGV) of the feedstock including diluent and reaction products within the reactor system can preferably be sufficient to fluidize the molecular sieve catalyst composition within a reaction zone in the reactor system. In one embodiment, the SGV in the process, particularly within the reactor system, more particularly within the reaction zone of the riser reactor(s), can be at least 0.1 meter per second (m/sec), preferably greater than about 0.5 m/sec, more preferably greater than about 1 m/sec, even more preferably greater than about 2 m/sec, yet even more preferably greater than about 3 m/sec, and most preferably greater than about 4 m/sec. See, for example, U.S. Pat. No. 6,552,240, the disclosure of which is hereby incorporated by reference.

According to one embodiment, the conversion of oxygenate, particularly the conversion of methanol, to form olefin(s) is from about 90 wt % to about 99.9 wt %. According to another embodiment, the conversion of methanol to olefin(s) is from about 92 wt % to about 99 wt %, typically from about 94 wt % to about 98 wt %.

According to another embodiment, the conversion of methanol to olefin(s) can be above about 98 wt % to less than about 100 wt %. According to another embodiment, the conversion of methanol to olefin(s) can be from about 98.1 wt % to less than about 100 wt %, or alternately from about 98.2 wt % to about 99.8 wt %. According to another embodiment, the conversion of methanol to olefin(s) can be from about 98.2 wt % to less than about 99.5 wt %, or alternately from about 98.2 wt % to about 99 wt %.

It can be desirable to maintain an amount of coke on the catalyst in the reaction vessel, e.g., to enhance the formation of desired olefin product, particularly ethylene and propylene. For instance, in one embodiment, it is particularly desirable that the level of coke on the catalyst in the reactor be at least about 1.5 wt %, preferably from about 2 wt % to about 30 wt %.

5. Impact of Ethylene-Propylene Ratio in OTO Reactions

It has been discovered that ethanol has a selectivity for ethylene under OTO and ETO (ethanol-to-olefins) reaction conditions, which approaches 100 weight percent. Methanol, in contrast, produces ethylene and propylene in generally equal amounts under OTO reaction conditions. By increasing the amount of alcohol that tends to produce higher quantities of ethylene in the OTO feedstock, the amount of ethylene produced in the OTO reaction system relative to propylene can be correspondingly increased. See, e.g., U.S. Patent Application Publication No. 2005-0107482, which is incorporated herein by reference in its entirety, for further discussion of ethylene-propylene ratio and its impact on OTO reaction processes, inter alia.

6. OTO Reaction Product Properties and Characteristics

The reaction of oxygenate(s) according to the invention, as facilitated by catalyst compositions according to the invention, inter alia, can advantageously produce an olefin-containing product according to the invention. This olefin-containing product can have various quantifiable properties and characteristics, which can depend on a number of factors including, but not limited to, reaction conditions (e.g., temperatures, pressures, WHSVs, flow rates, etc.), reactor geometry, chemical and/or physical nature of the catalyst composition, catalyst coking levels, catalyst regeneration conditions, oxygenate conversion, oxygenate composition, and the like, and combinations thereof. The aforementioned quantifiable properties and characteristics can include, but are in no way limited to, prime olefin selectivity, prime olefin ratio, impurity content (e.g., aldehydes, acids, alkanes, dienes and/or polyenes, alkynes, ketones, aromatic compounds, alkyl ethers, alkanols, unreacted oxygenates, unreacted syngas/natural gas components, catalyst fines, in some cases α-disubstituted olefins such as isobutylene, in some cases heavier olefins such as $C_6$+ olefins, and the like, and combinations thereof), and the like.

In one embodiment, the catalyst composition is chosen, in combination with the reaction system set-up and conditions, so that the catalyst composition has an on-stream catalyst lifetime of at least 50 grams methanol converted per gram of sieve, preferably at least 60 grams methanol converted per gram of sieve, for example at least 65 grams methanol converted per gram of sieve, at least 70 grams methanol converted per gram of sieve, at least 75 grams methanol converted per gram of sieve, or at least 80 grams methanol converted per gram of sieve. In one embodiment, the catalyst composition has an on-stream catalyst lifetime from 60 to 90 grams methanol converted per gram of sieve, for example from 60 to 80 grams methanol converted per gram of sieve, from 65 to 85 grams methanol converted per gram of sieve, from 70 to 90 grams methanol converted per gram of sieve, from 65 to 80 grams methanol converted per gram of sieve, or from 70 to 80 grams methanol converted per gram of sieve.

As used herein, the phrase "prime olefin selectivity" should be understood by one of ordinary skill in the art to mean the conversion-weighted average weight of ethylene and propylene produced in the reaction product divided by the weight of $CH_2$ groups in the oxygenate feed converted. As used herein, the phrase "prime olefin ratio" should be understood by one of ordinary skill in the art to mean the ratio of the conversion-weighted average yield of ethylene to the conversion-weighted average yield of propylene in the reaction product.

In one embodiment, the prime olefin selectivity (or POS) of the OTO reaction product according to the invention can be greater than 75%, preferably at least 75.5%, for example from 75.5% to 95%, from 76% to 90%, or from 76% to 85%, or alternately at least 76%.

In one embodiment, the prime olefin ratio (or POR) of the OTO reaction product according to the invention can be greater than 0.9:1, more preferably at least 1.0:1, for example at least 1.05:1, at least 1.1:1, at least 1.15:1, or at least 1.2:1. In one embodiment, the prime olefin ratio (or POR) of the OTO reaction product according to the invention can be less than 2.0:1, for example no more than 1.9:1, no more than 1.8:1, no more than 1.7:1, no more than 1.6:1, or no more than 1.5:1.

In one embodiment, the amount of aldehyde impurities, particularly the amount of acetaldehyde impurities, in the olefin-containing product can be less than about 20,000 wppm, preferably not more than about 15,000 wppm, for example not more than about 13,000 wppm, not more than about 11,500 wppm, not more than about 10,000 wppm, not more than about 9,000 wppm, not more than about 8,000 wppm, not more than about 7,000 wppm, not more than about 6,000 wppm, or not more than about 5,000 wppm, based on the total weight of the feedstock (including any diluent contained therein). In one embodiment, the amount of aldehyde impurities, particularly the amount of acetaldehyde impurities, in the olefin-containing product can be not less than about 500 wppm, for example not less than about 750 wppm, not less than about 1,000 wppm, not less than about 1,500 wppm, not less than about 2,000 wppm, not less than about 2,500 wppm, not less than about 3,000 wppm, not less than about 4,000 wppm, or not less than about 5,000 wppm.

D. OLEFIN PRODUCT RECOVERY AND USE

In one embodiment, olefin product and other gases can be withdrawn from the reactor and passed through a recovery system. Any recovery system, technique, and/or sequence useful in separating olefin(s) and purifying olefin(s) from other gaseous components can be used in this invention. Examples of recovery systems can include, but are not limited to, one or more or a combination of various separation, fractionation, and/or distillation towers, columns, splitters, other associated equipment (e.g. various condensers, heat exchangers, refrigeration systems or chill trains, compressors, knockout drums or pots, pumps, etc.), and the like, multiples, and combinations thereof.

Non-limiting examples of distillation towers, columns, splitters, or trains used alone or in combination can include one or more of a demethanizer (preferably a high temperature demethanizer), a deethanizer, a depropanizer (preferably a wet depropanizer), a wash tower often referred to as a caustic wash tower and/or quench tower, an absorber, an adsorber, a membrane, an ethylene ($C_2$) splitter, a propylene ($C_3$) splitter, a butene ($C_4$) splitter, and the like, multiples, and combinations thereof.

Various recovery systems useful for recovering predominately olefin(s), preferably prime or light olefin(s) such as ethylene, propylene, and/or butylene, are described, for example, in U.S. Pat. Nos. 5,960,643; 5,019,143; 5,452,581; 5,082,481; 5,672,197; 6,069,288; 5,904,880; 5,927,063; 6,121,504; 6,121,503; and 6,293,998; the disclosures of which are all fully incorporated herein by reference.

Generally, accompanying most recovery systems is the production, generation, and/or accumulation of additional products, by-products, and/or contaminants, along with the preferred products [e.g., prime olefin(s)]. The preferred prime products, i.e., light olefins such as ethylene and propylene, are typically purified for use in derivative manufacturing processes, such as polymerization processes. Therefore, in a preferred embodiment of the recovery system, the recovery system also includes a purification system. For example, the light olefin(s) produced, particularly in a MTO process, can be passed through a purification system that removes low levels of by-products and/or contaminants.

Non-limiting examples of contaminants and by-products include generally polar compounds, e.g., water, alcohols, carboxylic acids, ethers, carbon oxides, sulfur compounds (such as hydrogen sulfide, carbonyl sulfides, and mercaptans), ammonia and other nitrogenated compounds, arsine, phosphine, chlorides, and the like, and combinations thereof. Other contaminants and by-products can include, but are not limited to, hydrogen and hydrocarbons such as acetylene, methyl acetylene, propadiene, butadiene, butyne, and the like, and combinations thereof.

Other recovery systems including purification systems, for example for the purification of olefin(s), are described in *Kirk-Othmer Encyclopedia of Chemical Technology, 4th Edition*, Volume 9, John Wiley & Sons, 1996, pages 249-271 and 894-899, which is hereby incorporated by reference herein. Purification systems are also described in, for example, U.S. Pat. No. 6,271,428, U.S. Pat. No. 6,293,999, and U.S. patent application Ser. No. 09/689,363 filed Oct. 20, 2000, the disclosures of which are hereby incorporated by reference herein.

E. OLIGOMERIZATION/POLYMERIZATION OF OLEFIN PRODUCT

The ethylene and propylene streams produced and recovered according to this invention can be polymerized to form oligomeric, polymeric, and/or plastic compositions, e.g., polyolefins, particularly oligomers, homopolymers, copolymers, and/or blends of monomers, such as ethylene and propylene, formed by a process according to this invention. Any suitable process for forming polyethylene and/or polypropylene oligomers, homopolymers, copolymers, and/or blends can be used. Catalytic polymerization processes are typically preferred. Particularly preferred are metallocene, Ziegler/Natta, aluminum oxide, and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment, the ethylene or propylene product can be contacted with a metallocene catalyst to form an oligoolefin or a polyolefin (hereinafter, collectively "polyolefin"). In some embodiments, the polyolefin forming process can be carried out at a temperature from about 50° C. to about 320° C., and/or at low, medium, or high pressure, being anywhere from below about 1 barg (1.02 kg/cm$^2$ gauge) to about 3200 barg (3264 kg/cm$^2$ gauge). For processes desired to be carried out in solution, an inert diluent can be used. In this type of operation, it can be desirable that the pressure range from about 10 barg (10.2 kg/cm$^2$ gauge) to about 150 barg (1.53 kg/cm$^2$ gauge), and preferably at a temperature from about 120° C. to about 250° C. For gas phase processes, it can be desirable that the temperature generally be from about 60° C. to about 120° C., and that the operating pressure range from about 5 barg (5.1 kg/cm$^2$ gauge) to about 50 barg (51 kg/cm$^2$ gauge).

In addition to polyolefins, numerous other olefin derivatives may be formed from the olefin products (e.g., ethylene, propylene, and $C_{4+}$ olefins, particularly butylenes) manufactured according to the invention. The olefins manufactured according to the invention can also be used to synthesize such compounds as aldehydes, acids such as $C_2$-$C_{13}$ mono carboxylic acids, alcohols such as $C_2$-$C_{12}$ mono alcohols, esters that can be made from the $C_2$-$C_{12}$ mono carboxylic acids and the $C_2$-$C_{12}$ mono alcohols, linear alpha-olefins, vinyl acetate, ethylene dichloride and vinyl chloride, ethylbenzene, ethylene oxide, cumene, acrolein, allyl chloride, propylene oxide, acrylic acid, ethylene-propylene rubbers, acrylonitrile, trimers and dimers of ethylene and propylene, and the like, and blends and copolymers and combinations thereof. The $C_{4+}$ olefins, butylene in particular, are particularly suited for the manufacture of aldehydes, acids, alcohols, esters that can be made from $C_5$-$C_{13}$ mono carboxylic acids and $C_5$-$C_{13}$ mono alcohols, and linear alpha-olefins.

F. ADDITIONAL/ALTERNATE EMBODIMENTS

Embodiment 1

A process for converting an oxygenate feed to a light olefin product comprising:
  a) providing the oxygenate feed comprising a majority of methanol and from about 5 wt % to about 30 wt % of one or more $C_2$-$C_4$ alcohols;
  b) providing a catalyst composition comprising a SAPO catalyst and a basic metal oxide co-catalyst, wherein the SAPO catalyst comprises a CHA framework type, an AEI framework type, or both, and wherein the basic metal oxide co-catalyst absorbs more than 0.03 mg of $CO_2$ per square meter of co-catalyst surface area at about 100° C.; and c) contacting the oxygenate feed with the catalyst composition under conditions sufficient to convert at least a portion of the oxygenate feed to a light olefin product, wherein the catalyst composition has an on-stream catalyst lifetime of at least 60 g methanol converted per gram of sieve.

Embodiment 2

The process of embodiment 1, wherein a majority of the catalyst composition is the SAPO molecular sieve catalyst, which is an intergrowth of CHA and AEI framework types.

Embodiment 3

The process of any of the previous embodiments, wherein the basic metal oxide co-catalyst absorbs from 0.035 mg to 5 mg of $CO_2$ per square meter of co-catalyst surface area at about 100° C.

Embodiment 4

The process of any of the previous embodiments, wherein the basic metal oxide co-catalyst comprises a Group 2 metal oxide, a Group 4 metal oxide, hydrotalcite, or a combination thereof.

Embodiment 5

The process of any of embodiments 1-3, wherein the basic metal oxide co-catalyst comprises yttria.

Embodiment 6

The process of any of the previous embodiments, wherein the SAPO catalyst and the basic metal oxide co-catalyst are present in a ratio from about 3:2 to about 19:1.

Embodiment 7

The process of any of the previous embodiments, wherein the oxygenate feed comprises at least about 60 wt % methanol and from about 8 wt % to about 25 wt % $C_2$-$C_3$ alcohols.

Embodiment 8

The process of any of the previous embodiments, wherein the olefin product has (i) a prime olefin ratio of at least 1.0:1, (ii) a prime olefin selectivity of at least 75.5%, or (iii) both (i) and (ii).

Embodiment 9

The process of any of the previous embodiments, wherein the olefin product has (i) a prime olefin ratio of at least 1.1:1, (ii) a prime olefin selectivity of at least 76%, or (iii) both (i) and (ii).

Embodiment 10

The process of any of the previous embodiments, wherein the olefin product has an aldehyde content of less than about 15,000 wppm.

Embodiment 11

The process of any of the previous embodiments, wherein the olefin product has an aldehyde content of at least about 3,000 wppm.

Embodiment 12

The process of any of the previous embodiments, wherein the catalyst composition has an on-stream catalyst lifetime of at least 70 g methanol converted per gram of sieve.

Embodiment 13

The process of any of the previous embodiments, wherein the catalyst composition has an LEI from about 1.2 to about 15.

Embodiment 14

The process of any of the previous embodiments, wherein the catalyst composition is contacted with the oxygenate feed at a temperature from about 450° C. to about 580° C.

Embodiment 15

A process for forming olefin-containing (co)polymers from an oxygenate feed comprising the steps of:
converting the oxygenate feed to a light olefin product according to any of the previous embodiments;
polymerizing at least a portion of the light olefin product as monomer, optionally in combination with one or more other comonomers, under reaction conditions sufficient to polymerize at least 10 wt % of the total amount of monomers and other comonomers to form an olefin-containing (co)polymer product; and
optionally washing, isolating, and/or purifying said olefin-containing (co)polymer product to form an olefin-containing (co)polymer.

G. EXAMPLES

The present invention can be better understood in view of the following non-limiting examples, which should not be read in any way to unduly limit the scope of the invention, as defined by the appended claims.

Example 1

OTO Conversion of a Methanol/Ethanol Feed Using SAPO+Yttria

In Example 1, the oxygenates-to-olefins process used a methanol feed with varying amounts of ethanol over a particulate SAPO molecular sieve catalyst, which is a CHA/AEI intergrowth (EMM-2) and having an $Si:Al_2$ ratio of about 0.1, and separate particles of yttrium oxide as the Group 3 metal oxide co-catalyst. The relative proportion of molecular sieve catalyst to metal oxide in Example 1 was about 5:1. The presence of ethanol in the methanol feed can typically lead to elevated levels of acetaldehyde in the product, e.g., through dehydrogenation of the ethanol. Process conditions of about 475° C. reactor temperature and about 25 psig (0.17 MPag) reactor pressure were used, as well as a WHSV of about 100 $hr^{-1}$, based on methanol. Prime olefin (ethylene+propylene) selectivity and prime olefin ratio (ethylene-propylene ratio) results were obtained under these conditions and are shown in Table 1 below, along with the content of acetaldehyde impurity in the resultant product.

TABLE 1

| % Ethanol in Feed | POS [wt %] | | POR | | Acetaldehyde formed [wt %] | |
|---|---|---|---|---|---|---|
| | EMM-2 | EMM-2 + $Y_2O_3$ | EMM-2 | EMM-2 + $Y_2O_3$ | EMM-2 | EMM-2 + $Y_2O_3$ |
| 0 | 74.7 | 71.1 | 0.88 | 0.69 | 0.25 | 0.02 |
| 10 | 74.6 | 76.6 | 1.2 | 1.0 | 3.3 | 0.84 |
| 20 | 74.2 | 78.2 | 1.5 | 1.4 | 4.6 | 1.0 |

Table 1 indicates that POS did not change much with increasing ethanol content in the feedstock where there is no metal oxide co-catalyst. However, the use of a metal oxide co-catalyst in combination with the SAPO catalyst led to a significant increase in POS with increasing ethanol feed content.

Table 1 also indicates that POR increased steadily with increasing ethanol content in the feedstock, whether the metal oxide co-catalyst is present or not. In Example 1, the presence of metal oxide co-catalyst yielded reduced POR values compared to those of the SAPO catalyst alone.

Table 1 further indicates that the presence of ethanol in the feedstock significantly increases the acetaldehyde content in the product, but formation of this impurity can be significantly controlled through co-use of the metal oxide co-catalyst.

Example 2

Conversion Reaction of Ethanol/Trioxane Feed Over Yttria

About 10 mg calcined and pelletized $Y_2O_3$ was mixed uniformly with about 85 mg sand of the same pellet size. The mixture was packed into a fixed-bed microreactor and heated to about 475° C. under flowing nitrogen. The trioxane/ethanol mixture was then fed to the catalyst bed under about 2.8 bara (about 25 psig) pressure with a syringe pump at about 21 μL/min (WHSV of ethanol vs. $Y_2O_3$ was approximately 140 $hr^{-1}$). Trioxane was used as a co-feed agent, as it is a cyclic trimer of formaldehyde that can decompose to formaldehyde, e.g., upon heating. The effluent was sampled with a gas chromatograph (GC) equipped with an FID detector. Table 2 below shows ethanol conversion and product selectivity. The trioxane was quantitatively converted, as it is not expected to survive the reaction conditions. It is clear that ethanol conversion did not change significantly over about 20 minutes, which was the run length of the experiment.

The results in Table 2 show that, first of all, the basic metal oxide, $Y_2O_3$, was capable of dehydrating ethanol to form ethylene, much like a solid acid. Secondly, acetaldehyde was produced in significant quantity, apparently from dehydrogenation of ethanol. Thirdly, the co-fed formaldehyde (from trioxane) was apparently converted into methanol (MeOH) or dimethylether (DME).

Thus these results suggest four possible reactions, the combination of which may account for the observed product slate:
1. Dehydration of alcohol to form olefin;
2. Cannizzaro reaction, which looks like that turns formaldehyde into MeOH/DME and formic acid, with formic acid decomposing to $CO_2$ and $H_2$, which were not detectable with the FID detector;
3. Dehydrogenation of alcohol to form aldehyde/ketone; and
4. Meerwein-Ponndorf-Verley-(MPV-) type reduction of formaldehyde with alcohol to produce methanol/DME and aldehyde/ketone, which looks like Based on the experimental data, but without being bound by theory, it can be concluded that Reaction 1 most likely takes place, as there is no other mechanism apparent at this

TABLE 2

| Time on Feed (Minutes) | Ethanol Conversion (Wt %) | Selectivity (Wt %) | | | | | | |
|---|---|---|---|---|---|---|---|---|
| | | MeOH/DME | CH3CHO | CH4 | C2H4 | C3H6 | C3-C4 Oxygenates | C4-C7 |
| 0.15 | 35.5 | 32.4 | 19.5 | 0.2 | 30.9 | 0.4 | 4.5 | 11.8 |
| 0.20 | 34.8 | 32.8 | 20.0 | 0.2 | 29.6 | 0.4 | 4.6 | 12.1 |
| 0.30 | 35.5 | 31.5 | 20.1 | 0.2 | 27.3 | 0.3 | 8.0 | 12.4 |
| 0.50 | 33.0 | 33.5 | 22.9 | 0.2 | 26.0 | 0.3 | 4.3 | 12.5 |
| 0.80 | 32.8 | 33.8 | 23.4 | 0.2 | 25.3 | 0.3 | 4.2 | 12.5 |
| 1.20 | 32.0 | 34.0 | 24.9 | 0.2 | 23.9 | 0.3 | 4.1 | 12.4 |
| 1.70 | 32.1 | 34.4 | 25.1 | 0.2 | 23.8 | 0.3 | 4.1 | 11.9 |
| 2.30 | 32.1 | 34.1 | 25.4 | 0.2 | 24.0 | 0.3 | 4.1 | 11.7 |
| 3.00 | 31.7 | 34.0 | 26.4 | 0.2 | 23.0 | 0.3 | 4.2 | 11.7 |
| 4.00 | 31.5 | 34.3 | 27.0 | 0.1 | 22.1 | 0.2 | 4.1 | 11.9 |
| 5.50 | 31.8 | 34.1 | 26.7 | 0.1 | 22.4 | 0.2 | 4.1 | 12.0 |
| 8.00 | 31.6 | 34.1 | 27.7 | 0.1 | 21.6 | 0.2 | 4.1 | 11.8 |
| 11.00 | 32.9 | 32.7 | 26.8 | 0.1 | 20.8 | 0.2 | 7.6 | 11.5 |
| 15.00 | 32.7 | 32.5 | 27.9 | 0.1 | 20.2 | 0.2 | 7.3 | 11.5 |
| 20.00 | 33.2 | 32.4 | 27.9 | 0.1 | 20.1 | 0.2 | 7.1 | 11.9 | time to satisfactorily account for ethylene formation. Based on this experiment, however, Reactions 2-4 cannot merely be ruled out, as a combination of Reactions 2-3 can produce methanol/dimethylether and acetaldehyde, as can Reaction 4 as well. Clear evidence for MPV-type reaction at work comes from the following Example.

Example 3

Conversion Reaction of Isopropanol/Trioxane Feed Over Yttria

The same experiment of Example 1 was repeated, but the feed was replaced with either pure isopropanol (IPA) or a mixture of about 10 wt % trioxane and about 90 wt % IPA. IPA conversion with time and (major) product selectivity with both feeds are shown in FIGS. 1a-d.

The pure IPA case produced both dehydration and dehydrogenation products (propylene and acetone), which, again without being bound by theory, essentially confirms that Reactions 1 and 3 are both likely to be operative. The co-feed experiment of Example 3 also produced results similar to those in Example 2. In Example 2, MeOH/DME and acetone were formed, in addition to the dehydration product propylene. The comparison of the selectivity for acetone with the two feeds of Examples 2-3 is noteworthy—acetone selectivity was much higher with trioxane co-feed. This comparison suggests that MPV-type reduction (Reaction 4) of formaldehyde with IPA was taking place, because, on one hand, a boost of acetone with formaldehyde co-feed is expected of an MPV-type reduction reaction, and, on the other, there is no reason to expect that dehydrogenation due to Reaction 3 would necessarily increase in the presence of formaldehyde (trioxane).

Examples 2-3 above show that formaldehyde (from trioxane) can be converted to benign molecules, such as methanol or dimethyl ether, with the aid of alcohols co-fed over metal oxides, such as $Y_2O_3$. The co-fed alcohol can be quickly or simultaneously converted to an aldehyde or a ketone, most likely through a MPV-type reduction reaction mechanism.

The beneficial effect of co-feeding higher alcohols in methanol-to-olefins reactions using an aluminum- and phosphorus-containing catalyst, in combination with metal oxide co-catalyst, can be seen from the following Example.

Example 4

OTO Conversion of Various Methanol-Containing Feeds Using SAPO+Yttria

The same experimental set-up of Example 1 was used, but the catalyst was either a SAPO (in this case, a AEI/CHA intergrowth) or a mixture of about 90 wt % SAPO and 10 wt % $Y_2O_3$, and the feed was either pure methanol or a mixture of about 90 wt % to about 95 wt % methanol and about 5 wt % to about 10 wt % of an aldehyde or higher alcohol. The feed rate was such that the WHSV of methanol, with respect to the SAPO, was 100 $hr^{-1}$ for all experiments in this Example. The temperature of the reactor was about 475° C., and the pressure was about 2.8 bara (about 25 psig). Under such conditions, the initial methanol conversion was at or near about 100%, and this level of conversion was maintained for some time, before it eventually dropped to 10%. The total amount of methanol converted, until the point of 10% conversion, was integrated and normalized against the amount of SAPO catalyst loaded in the reactor. This on-stream catalyst lifetime, expressed as grams of methanol converted per gram of sieve, is shown in FIG. 2 for the various feed compositions.

Figure 1A:
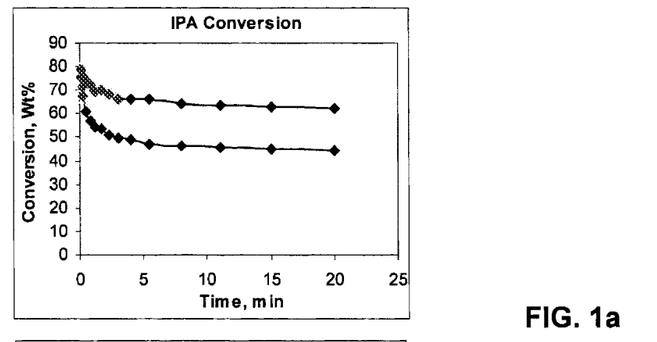
FIG. 1a shows a graph of the oxygenate conversion vs. time for two oxygenate feeds over a metal oxide hydrocarbon conversion catalyst.
Figure 1B:
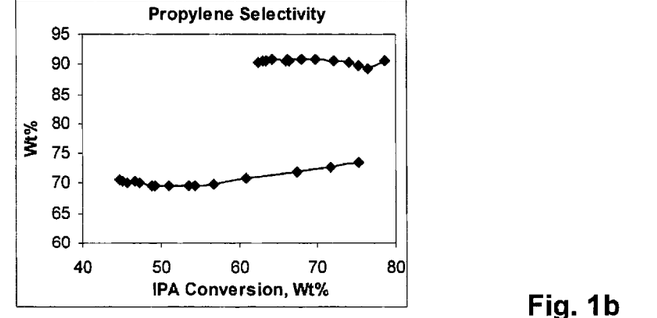
FIG. 1b shows a graph of the propylene selectivity vs. oxygenate conversion for two oxygenate feeds over a metal oxide hydrocarbon conversion catalyst.
Figure 1C:
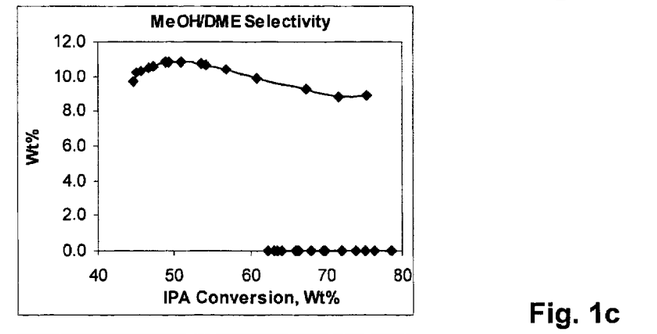
FIG. 1c shows a graph of the MeOH/DME selectivity vs. oxygenate conversion for two oxygenate feeds over a metal oxide hydrocarbon conversion catalyst.
Figure 1D:
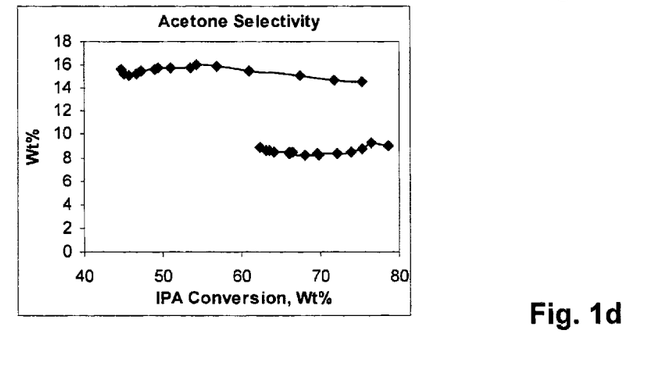
FIG. 1d shows a graph of ketone selectivity vs. oxygenate conversion for two oxygenate feeds over a metal oxide hydrocarbon conversion catalyst.
Figure 2:
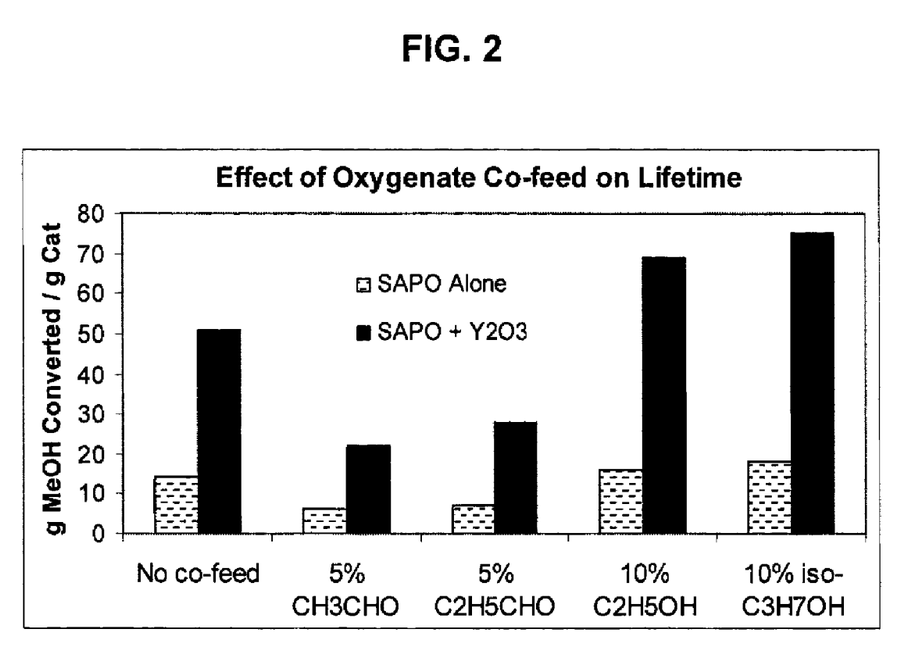
FIG. 2 shows a graph of on-stream catalyst lifetime for a variety of methanol-containing oxygenate feeds over two SAPO-containing hydrocarbon conversion catalyst compositions.

The results shown in FIG. 2 indicate that co-feeding higher alcohols (the two sets of bars on the right) with methanol further improved the beneficial effect of metal oxide in prolonging the on-stream lifetime of MTO catalyst. It can also be seen from FIG. 2 that co-feeding of aldehydes, such as acetaldehyde or propaldehyde, did the opposite. It was proposed that these molecules are also contributors to coke formation, much like formaldehyde but with less potency. Therefore, these results seem consistent with those shown in Examples 2-3. Without being bound by theory, it is believed that the co-fed higher alcohols assisted in the interception of formaldehyde (in whatever form), converting it into benign methanol, probably via an MPV-type reduction reaction, during which the higher alcohols themselves are converted into aldehydes and/or ketones, which are believed to be much less potent vis-à-vis MTO catalyst deactivation.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:
1. A process for converting an oxygenate feed to a light olefin product comprising:
   a) providing the oxygenate feed comprising a majority of methanol and from about 8 wt % to about 30 wt % of one or more $C_2$-$C_4$ alcohols;
   b) providing a catalyst composition consisting of a SAPO catalyst and a basic Group 3 metal oxide co-catalyst at a SAPO catalyst to basic Group 3 metal oxide co-catalyst ratio from about 10:1 to about 2:1, wherein the SAPO catalyst comprises a CHA framework type, an AEI framework type, or both, and wherein the basic metal oxide co-catalyst absorbs more than 0.03 mg of $CO_2$ per square meter of co-catalyst surface area at about 100° C.; and
   c) contacting the oxygenate feed with the catalyst composition at a temperature from about 450° C. to about 580° C. and other under conditions sufficient to convert at least a portion of the oxygenate feed to a light olefin product, wherein the catalyst composition has an on-stream catalyst lifetime of at least 60 g methanol converted per gram of sieve;
   wherein the olefin product has (i) a prime olefin ratio of at least 1.0:1, (ii) a prime olefin selectivity of at least 75.5%, or (iii) both (i) and (ii).

2. The process of claim 1, wherein a majority of the catalyst composition is the SAPO molecular sieve catalyst, which is an intergrowth of CHA and AEI framework types.

3. The process of claim 1, wherein the basic metal oxide co-catalyst absorbs from 0.035 mg to 5 mg of $CO_2$ per square meter of co-catalyst surface area at about 100° C.

4. The process of claim 1, wherein the basic metal oxide co-catalyst comprises yttria.

5. The process of claim 1, wherein the oxygenate feed comprises at least about 60 wt % methanol and from about 8 wt % to about 25 wt % $C_2$-$C_3$ alcohols.

6. The process of claim 1, wherein the olefin product has (i) a prime olefin ratio of at least 1.1:1, (ii) a prime olefin selectivity of at least 76%, or (iii) both (i) and (ii).

7. The process of claim 1, wherein the olefin product has an aldehyde content of less than about 15,000 wppm.

8. The process of claim 7, wherein the olefin product has an aldehyde content of at least about 3,000 wppm.

9. The process of claim 1, wherein the catalyst composition has an on-stream catalyst lifetime of at least 70 g methanol converted per gram of sieve.

10. The process of claim 1, wherein the catalyst composition has an LEI from about 1.2 to about 15.

11. The process of claim 1, wherein between about 20,000 wppm and about 2,000 wppm of acetaldehyde is provided.

* * * * *